United States Patent [19]
Sanders

[11] Patent Number: 5,888,211
[45] Date of Patent: *Mar. 30, 1999

[54] BIPOLAR-UNIPOLAR ADAPTOR FOR A HEAD TRIAL

[75] Inventor: Anthony P. Sanders, Lakeville, Mass.

[73] Assignee: Johnson & Johnson Professional, Inc., Raynham, Mass.

[ * ] Notice: The term of this patent shall not extend beyond the expiration date of Pat. No. 5,800,556.

[21] Appl. No.: 910,617

[22] Filed: Aug. 13, 1997

Related U.S. Application Data

[63] Continuation-in-part of Ser. No. 652,764, May 23, 1996, Pat. No. 5,800,556.

[51] Int. Cl.⁶ .................................................. A61F 2/36
[52] U.S. Cl. ................... 623/23; 606/91; 606/102
[58] Field of Search .................. 623/18, 19, 22, 623/23; 606/81, 91, 102

[56] References Cited

U.S. PATENT DOCUMENTS

| | | | |
|---|---|---|---|
| 5,108,452 | 4/1992 | Fallin | 623/23 |
| 5,156,624 | 10/1992 | Barnes | 623/22 |
| 5,156,626 | 10/1992 | Broderick et al. | 623/22 |
| 5,358,524 | 10/1994 | Richelsoph | 623/16 |
| 5,383,938 | 1/1995 | Rohr et al. | 623/22 |
| 5,405,394 | 4/1995 | Davidson | 623/18 |
| 5,569,263 | 10/1996 | Hein | 606/102 |
| 5,645,607 | 7/1997 | Hickey | 623/23 |
| 5,658,340 | 8/1997 | Müller et al. | 623/19 |

*Primary Examiner*—Mickey Yu
*Assistant Examiner*—Bruce E. Snow
*Attorney, Agent, or Firm*—Nutter, McClennen & Fish, LLP

[57] ABSTRACT

A femoral head trial adaptor for converting a shell trial to a head trial includes a barrel member having an outer surface and an inner surface defining a cavity for receiving a femoral neck trial. A circumferential flange portion is located on the outer surface of the barrel member. A resilient connecting member disposed on the circumferential flange has a nominal first diameter compressible to a smaller second diameter in response to a force and returnable to the first diameter in the absence of the force for securing the trial adaptor to a shell trial. The flange may be located at a predetermined position along the outer surface of the barrel member so as to simulate a neck trial of a given length.

25 Claims, 6 Drawing Sheets

BIPOLAR-UNIPOLAR ADAPTOR FOR A HEAD TRIAL

CROSS-REFERENCE TO RELATED APPLICATION

This application is a continuation-in-part of U.S. Ser. No. 08/652,764, filed May 23, 1996, now U.S. Pat. No. 5,800,556.

FIELD OF THE INVENTION

The present invention relates to an adaptor for converting a bipolar shell trial into a unipolar head trial.

BACKGROUND OF THE INVENTION

A successful hip replacement or arthroplasty procedure results, in part, from selection of prosthetic joint components that are dimensioned and positioned to closely approximate or replicate the geometry and functional characteristics of a natural, healthy hip joint. Typically, the component selection process includes a pre-operative analysis of joint images. The component selection process also includes temporary fixation of one or more provisional components to a bone or bones of interest prior to permanent fixation of the prosthetic joint. The provisional components are intended to mimic certain aspects of the permanent prosthetic joint in order for a surgeon to validate measurements and to test or "tryout" several different component sizes and configurations. Hence, provisional components are aptly known as "trials."

In a known procedure, a trial for a hip femoral component is used in the following manner. The proximal end of a femur is resectioned and the medullary canal of the femur is reamed. A broach is inserted into the resectioned proximal end of the femur to provide a cavity within the bone dimensioned and contoured to receive a femoral stem. Prior to removing the broach, a trial neck or trunnion and trial head can be secured to the broach to simulate a complete femoral stem. Normally, several neck and head trials of varying lengths and geometries are successively joined to the broach in an attempt to determine an appropriate neck length and overall femoral stem length. Once these lengths have been determined, the trial neck and head are removed from the broach and the broach is removed from the femur. Subsequently, a femoral stem of the appropriate length is selected for insertion into the cavity defined by the broach using techniques known to those skilled in the art.

Two types of femoral prostheses are typically suitable for hip arthroplasty procedures. One type is a bipolar prosthesis. In general, a bipolar hip prosthesis includes a shell having an external surface which articulates with the acetabulum and an internal surface which articulates with the spherical head member of a prosthetic femoral component. The other type of prosthesis is often referred to as a unipolar endoprosthesis in which the prosthetic femoral component includes a spherical head member which is large enough to articulate directly with the acetabulum.

U.S. Pat. No. 5,156,626 describes a procedure used to implant a bipolar hip prosthesis utilizing a four piece trial reduction system. This system includes a femoral broach trial, a neck portion attached to the broach, a head trial attached to the neck, and a shell for receiving the head trial and fitting within the acetabulum of a patient. The trial procedure using these four pieces can be at times cumbersome for the physician because the head can tend to dislocate and move out of the shell when the physician is attempting to place the trial into position. In addition, the trial system requires the use of numerous parts that must be selected and mated in various combinations.

Unipolar trial systems used in implanting unipolar hips typically comprise a broach, neck, and head trial. Unipolar trial counterpart pieces could be used in some situations to perform the trial reduction of bipolar hip implants because one of the primary interests in performing a trial reduction in both bipolar and unipolar implant procedures is to determine device fit (i.e., shell or head) in the acetabulum. Also, in many cases, the range of motion of the bipolar implant can be approximated with a unipolar trial.

SUMMARY OF THE INVENTION

The present invention overcomes the disadvantages of known femoral trials by providing a bipolar to unipolar head trial adaptor that may be inserted into or removed from a bipolar shell to convert the bipolar shell trial into a unipolar head.

One embodiment of the adaptor further provides an adjustable neck that eliminates the necessity for multiple unipolar head trials corresponding to different neck lengths for each of the different possible head sizes. A preferred version of this embodiment provides a spring loaded snap-in adaptor and a quick release neck length adjusting mechanism.

The invention also provides a fixed length femoral head trial adaptor system. The fixed length trial adaptor includes a cylindrical barrel member having an internal cavity shaped to receive a neck trunnion from a femoral stem trial. The adaptor also includes a circumferential flange on the outer surface of the barrel having a resilient connecting element disposed thereon. The connecting element, which secures the adaptor to the shell trial, has a nominal first diameter which is compressible to a smaller second diameter in response to a force. When the compressive force is removed, the connecting element resumes its first diameter.

In a preferred embodiment, the connecting element is shaped so as to mate with an annular groove provided within the shell trial.

In a preferred embodiment, the circumferential flange is located at a predetermined position on the outer surface of the barrel member and the internal cavity has a predetermined depth so as to simulate a given neck trunnion length. In this manner, a plurality of adaptors, each representing different neck lengths, may be employed in a trial system.

DETAILED DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
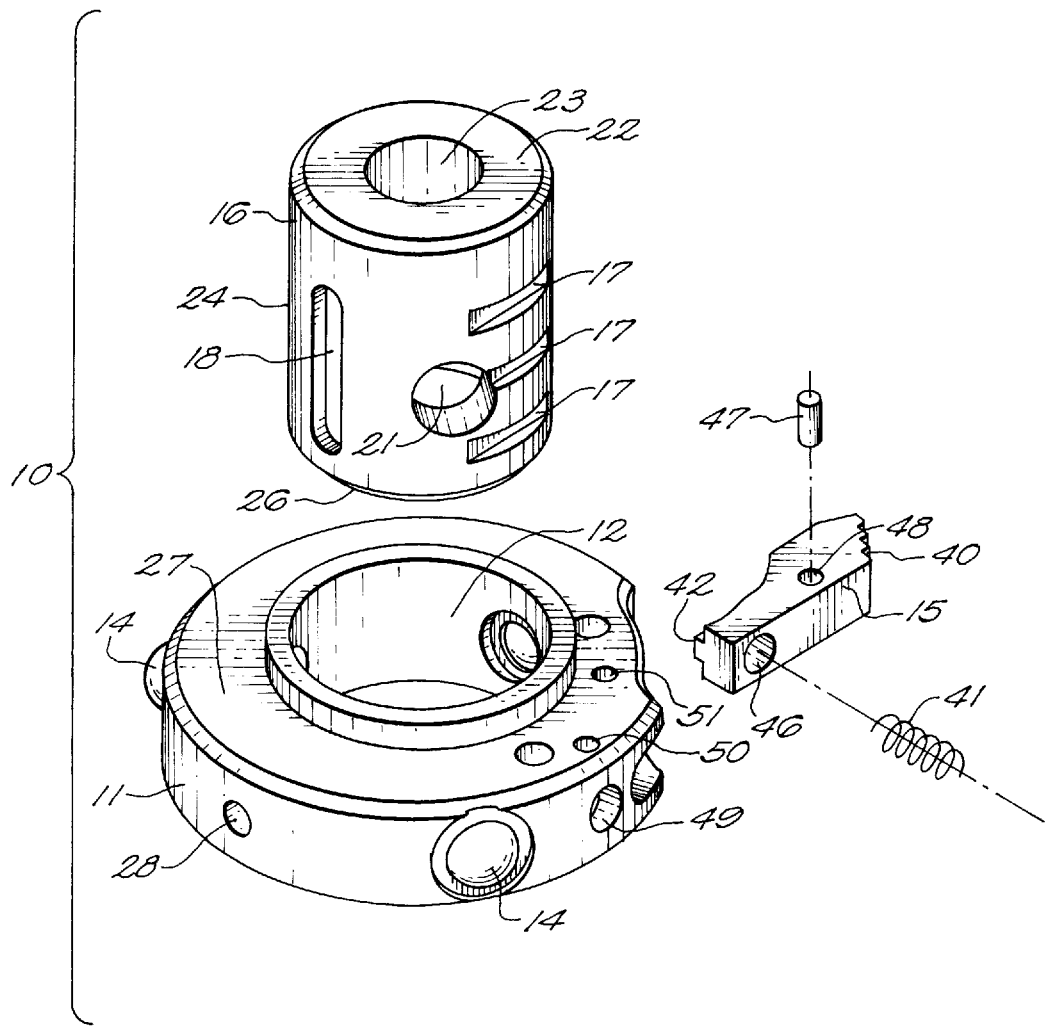
FIG. 1 is an exploded perspective view of a trial adaptor of the present invention having an adjustable neck length.
Figure 2:
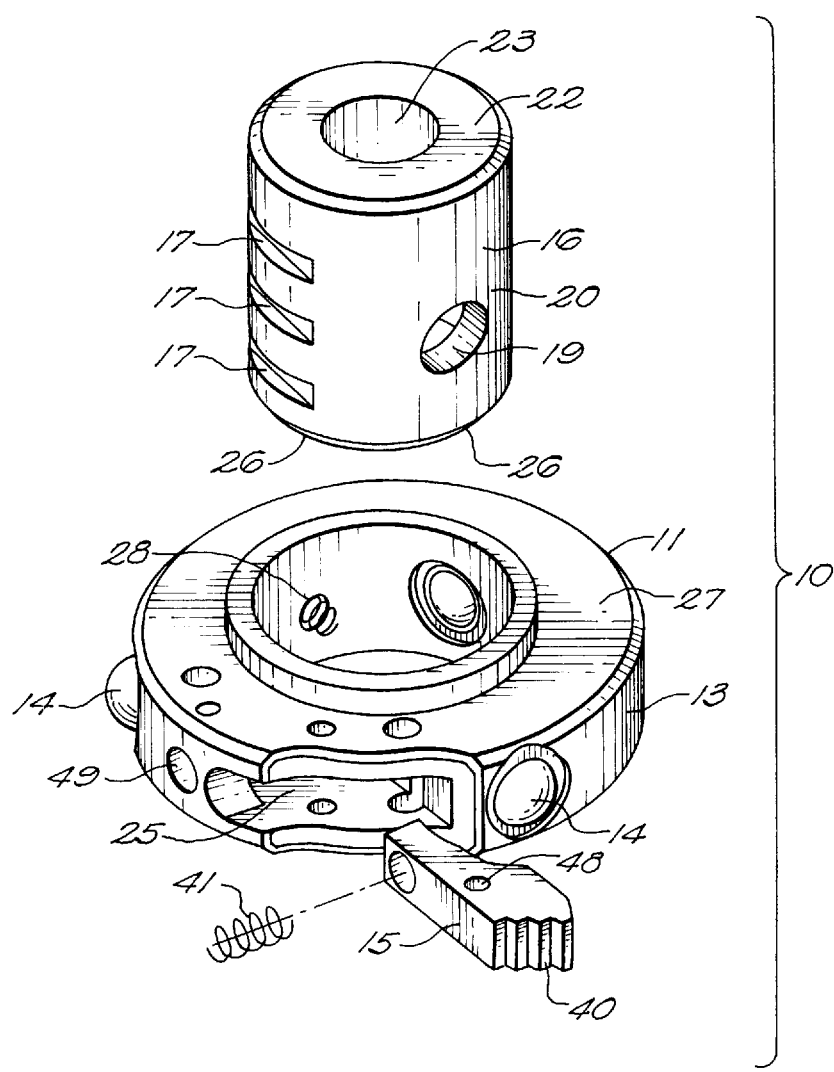
FIG. 2 is an exploded perspective view of the trial adaptor of the FIG. 1 rotated approximately ninety degrees.
Figure 3:
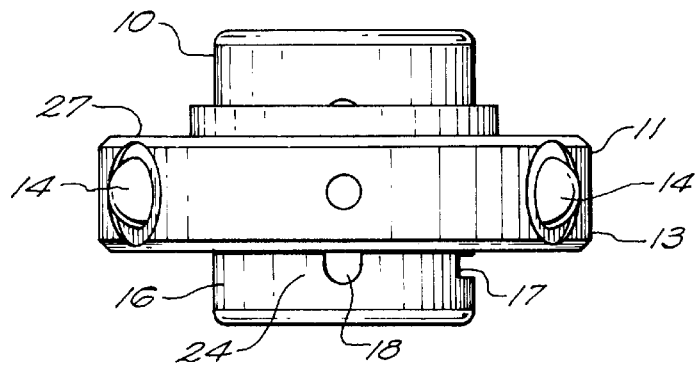
FIG. 3 is a side view of the trial adaptor of FIG. 1.

An adjustable trial adaptor 10 of the invention is illustrated in FIGS. 1–3. The adjustable trial adaptor 10 includes a cylindrical portion 11 having an opening 12 extending therethrough, spring loaded ball plungers 14 extending from the outer circumference 13 of the cylindrical portion 11 and a pawl 15 extending through the outer circumference 13 of the cylindrical portion 11 partially into opening 12.

The trial adaptor further includes a barrel 16 which acts as the adjustable neck portion of a unipolar head trial when the adaptor 10 is inserted into a bipolar shell. The barrel 16 comprises three grooves 17 in the outer circumference of the barrel 16. The barrel 16 further comprises a longitudinal slot 18 on the outer circumference 24 of the barrel 16, and openings 19 extending through the cylindrical wall 20 of the barrel. The barrel 16 comprises a longitudinal opening 21 extending from the bottom 26 of the barrel to a top wall 22 of the barrel. The top wall 22 includes a smaller opening 23 continuous with the opening 21.

A dowel pin 28 is press fit through the side of the cylindrical portion 11 and extends into capture slot 18 of barrel 16. The pin 28 movably secures the cylindrical portion 11 to the barrel 16 while the capture slot 18 permits the barrel 16 to move up and down between the three neck length positions defined by the grooves 17.

The pawl 15 comprises a button portion 40, a groove engaging portion 42, and a blind hole 46 for receiving compression spring 41. When assembled the pawl 15 is inserted into the opening 25 and is rotatably coupled to the cylindrical portion 11 with a dowel pin 47 press fit through hole 51 in cylindrical portion 11 and through hole 48 in pawl 15. The compression spring 41 is inserted into the hole 49 in the cylindrical portion 11 and into hole 46 in pawl, aligned with hole 49 of cylindrical portion 11. A dowel pin 50 extends into cylindrical portion 11 across hole 49 to capture the spring 41 in a compressed state in holes 46, 49. The pawl 15 is biased by spring 41 towards the barrel 16 so that when the barrel 16 is in a locked position, the groove engaging portion 42 extends into one of the grooves 17. The button portion 40 is exposed at the outer circumference 13 of the cylindrical portion 11 so that a user may actuate the button 40 to release the engaging portion 42 from engagement with the groove 17 and move the barrel 16 into a desired position.

Figure 4:
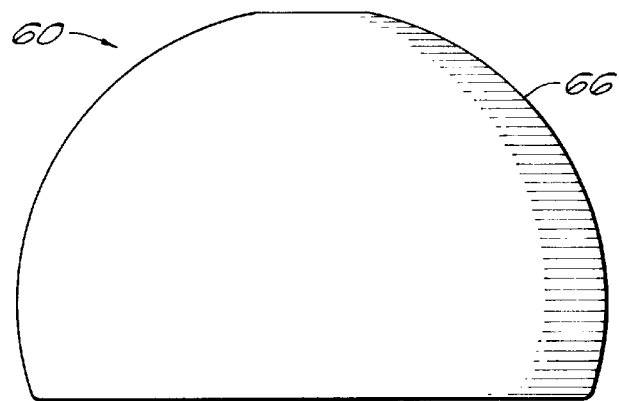
FIG. 4 is a side view of a bipolar shell trial.
Figure 4A:
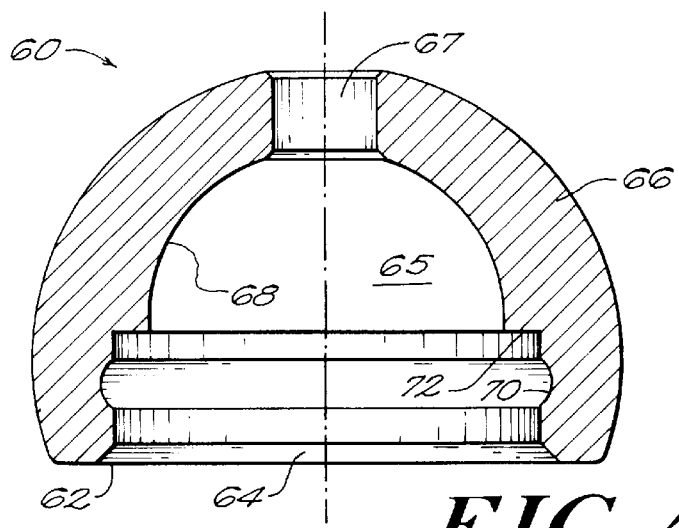
FIG. 4A is a cross-sectional view of the bipolar shell trial of FIG. 4.
Figure 5:
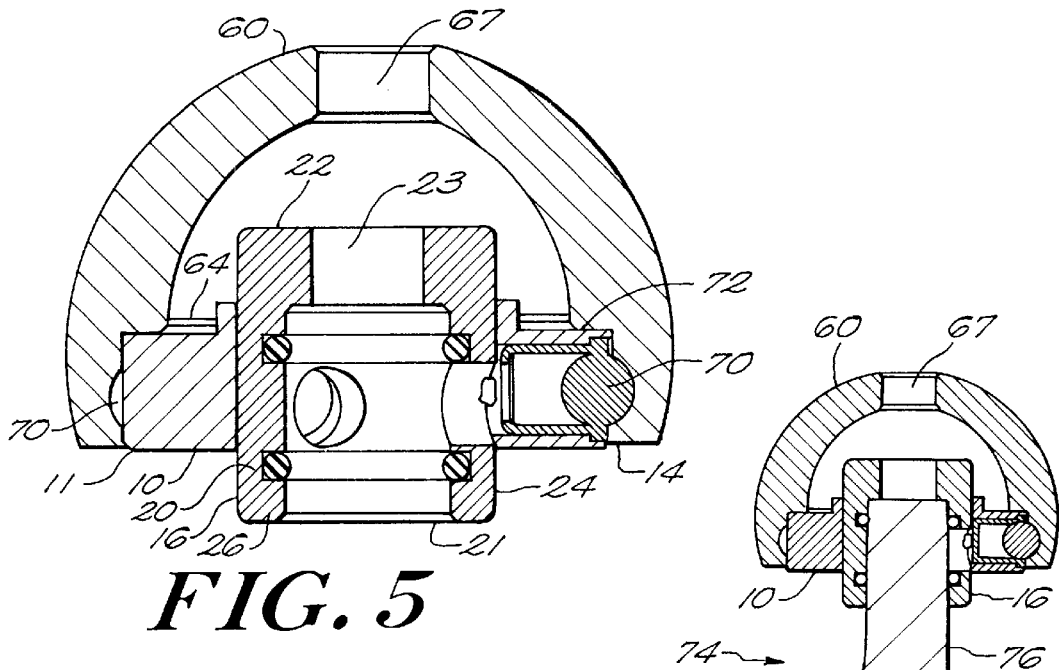
FIG. 5 is a cross sectional view of the trial adaptor of FIG. 1 in use with a bipolar shell trial.

A bipolar shell trial 60, shown in FIGS. 4 and 4A, and further shown mated to the adaptor 10 in FIG. 5, is spherically shaped with a flat inferior region 62.

An adaptor-receiving opening 64 is formed in the flat inferior region 62. A bone-contacting outer surface 66 of the shell trial 60 articulates with an acetabulum. The shell trial 60 is provided with a second, apical opening 67 which may be used to access the interior of the shell trial 60. Generally, the bipolar shell trial 60 is available in a variety of sizes having an outer diameter ranging from about 38 to 63 millimeters and a height ranging from about 27.5 to 40 millimeters.

The shell trial 60 also has an inner, non-bone contacting surface 65 that defines a cavity extending internally within the shell 60 from the opening 64. The inner surface 65 includes a hemispherical region 68 which may articulate with a head trial in a bipolar trial reduction that does not use an adaptor of the invention. Accordingly, a single shell trial component 60 may be used either in a bipolar trial, or with an adaptor of the invention as a head trial.

The inner surface 65 of shell trial 60 also defines an annular groove 70 and an annular shelf 72 which engage an adaptor, such as the trial adaptor 10, in concert to positively seat and retain the adaptor. The annular groove 70 is located internally to the adaptor receiving opening 64 and is shaped to accept a connecting element on a trial adaptor such as the spring loaded ball plungers 14 of trial adaptor 10. The annular shelf 72, also located within the opening 64, provides a positive seating means for the trial adaptor 10 with respect to the shell trial 60.

The shell trial 60 may be constructed from any material useful for temporary surgical use. Such materials include a variety of copolymers, particularly acetal copolymers, but also including polymeric material such as polyethylene, polypropylene, polyphenyl sulfone and nylon.

In use, as illustrated in FIG. 5, a trial adaptor 10 is inserted into the shell trial 60. The cylindrical portion 11 is inserted into the adaptor-receiving opening 64 in a bipolar shell trial 60 with the barrel 16 extending down from the adaptor 10. The top portion 27 of the cylindrical portion 11 abuts against shelf 72, and spring loaded ball plungers 14 fit into the groove 70 formed within the bipolar shell trial 60. Thus, the adaptor may be snapped into place within the bipolar shell trial 60 and held there by spring loaded ball plungers 14 that extend into groove 70.

Figure 6:
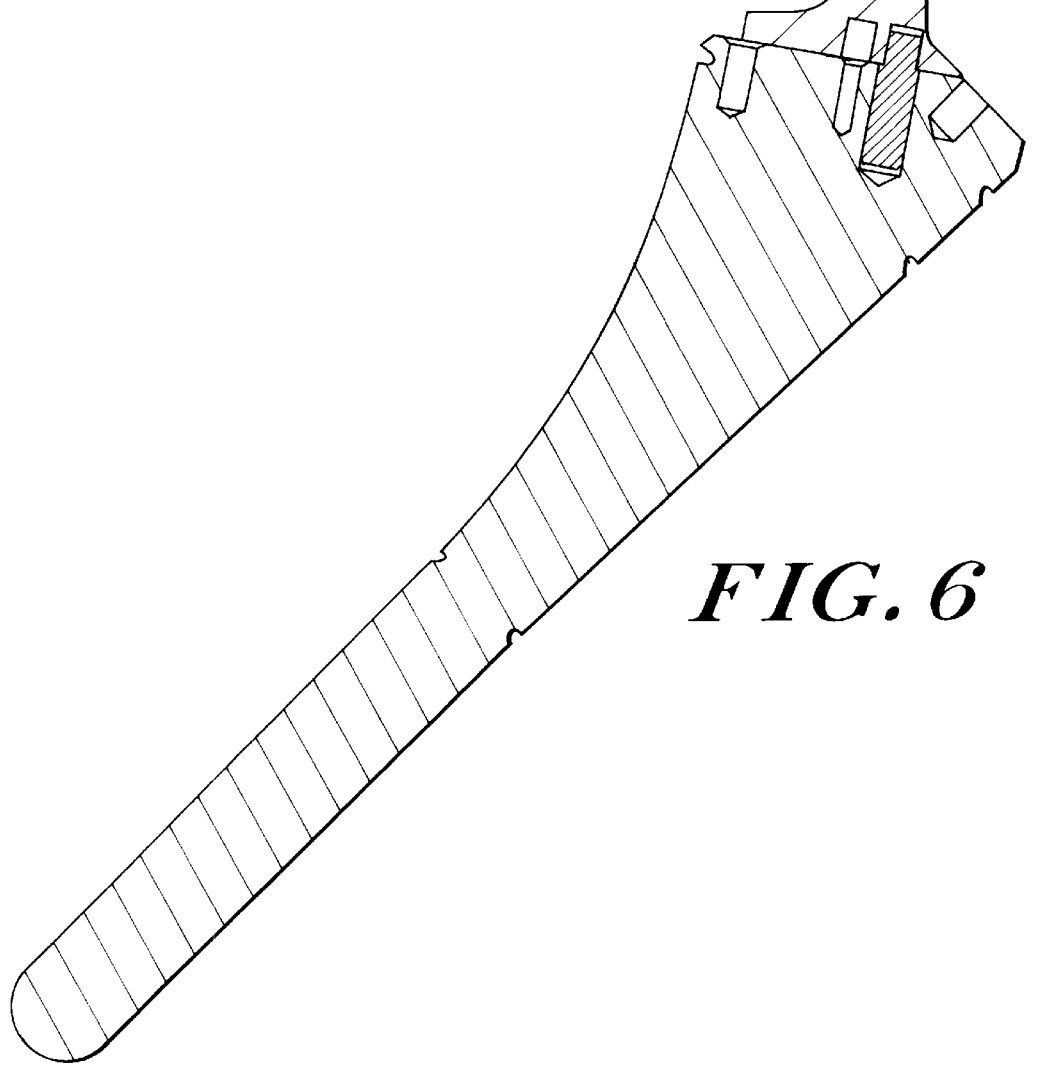
FIG. 6 is a cross-sectional view of a femoral trial system of the invention.
Figure 7:
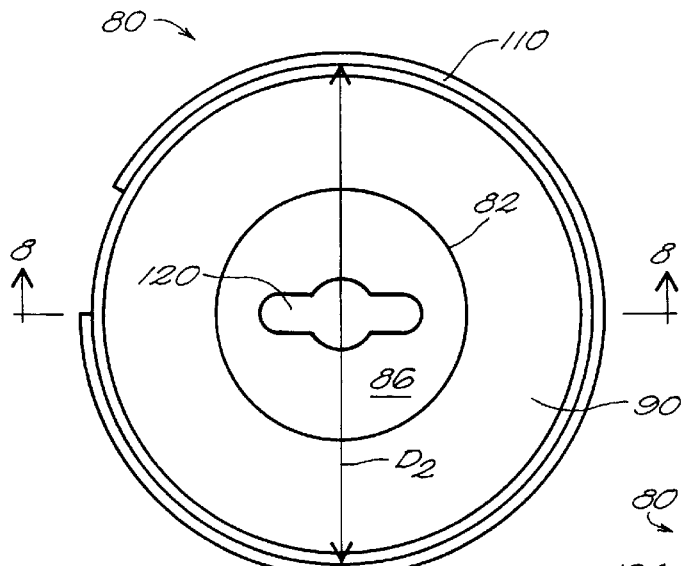
FIG. 7 is a top or superior view of a fixed length adaptor of the invention.
Figure 8:
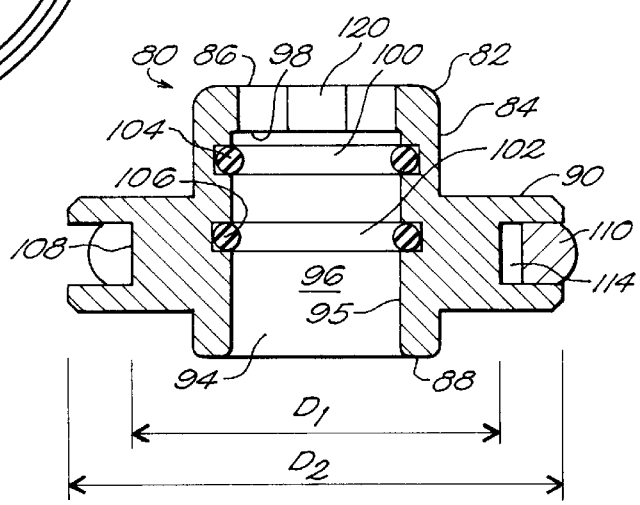
FIG. 8 is a cross-sectional view of the adaptor of FIG. 7 taken along line 8—8.

As shown in FIG. 6, the barrel 16 acts as an interface for a femoral neck trunnion 76 of the femoral trial 74. The femoral neck trunnion 76 may be coupled to the adaptor 10 by inserting it into the opening 21 in the barrel 16.

As assembled, the barrel 16 is inserted into the opening 12 of the cylindrical portion 11. The grooves 17 serve to engage with the pawl 15 to lock the barrel 16 into a selected position corresponding to a desired neck length. Thus the adaptor is arranged to extend the neck length of the femoral trial. The three grooves 17 correspond to three different neck lengths, for example, to zero, five and ten millimeter neck lengths.

The button portion 40 of the pawl 15 is activated to release the engaging portion 42 from the groove 17 engaged by the pawl 15. The barrel 16 is extended to a position so that the neck portion 45 of the femoral trial 44 when attached to the barrel 16 will be at a desired length. The button portion 40 is then released causing the pawl 15 to engage the groove 17 adjacent the pawl 15, locking the barrel 16 into the desired position.

The adjustable neck feature may be incorporated into any trial system whether it be a unipolar, bipolar, etc. system. The adjustable neck may be included with an adaptor as described or with any head or neck portion of a trial system.

The unipolar adaptor 10 may be disassembled from the bipolar shell trial 30 by pushing through the shell trial's apical hole 67 with any small diameter cylindrical instrument at hand.

Alternatively, a fixed length trial adaptor 80, illustrated in FIGS. 7 through 11C, may be employed in place of the adjustable trial adaptor 10. The fixed length trial adaptor 80 includes a generally cylindrical barrel member 82 having an outer surface 84 and superior and inferior ends 86, 88. A circumferential flange portion 90 is integral with the outer surface 84 of the barrel member between the superior and inferior ends 86, 88. The flange portion 90 is generally cylindrical, is smaller in height than the barrel member 82 and extends radially outward from the outer surface 84 of barrel member 82 to an outer diameter $D_2$.

The barrel member 82 has an inferior opening 94 and an inner surface 95 that defines a cavity 96 extending inwardly from the opening 94. The cavity 96 is adapted to seat a femoral neck trial. The internal cavity 96 is generally cylindrical and extends from the inferior opening 94 superiorly to an end region 98 against which a femoral neck trunnion abuts. The cavity 96 may be tapered so as to fit conventional neck trial trunnions which are also tapered. One of ordinary skill in the art will radily understand that various tapers can be used. Common tapers include $10/12$ and $11/13$ sizes in which the two numbers in each size designation represent the diameter of the neck measured at two different points along its length.

Grooves 100, 102 may be provided within the cavity 96 for seating one O-ring 104, 106 each. The O-rings 104, 106, which are preferably formed from a silicone rubber material, allow the adaptor 80 to mate snugly with a neck trial trunnion even where dimensions of the trunnion vary from a trial to a permanent prosthesis or among different manufacturers who may have different standards for measuring or sizing the tapers. In addition, the O-rings allow the mating between the neck and adaptor 80 to take place at two points along the length of the cavity 96. This configuration is preferable to direct mating along the length of the cavity 96 which can make it difficult to remove the trial adaptor 80 from the neck. As an alternative to O-rings, it is also possible to use at least one raised circumferential ridge (not shown) within the cavity 96 for the same purpose.

Figure 9:
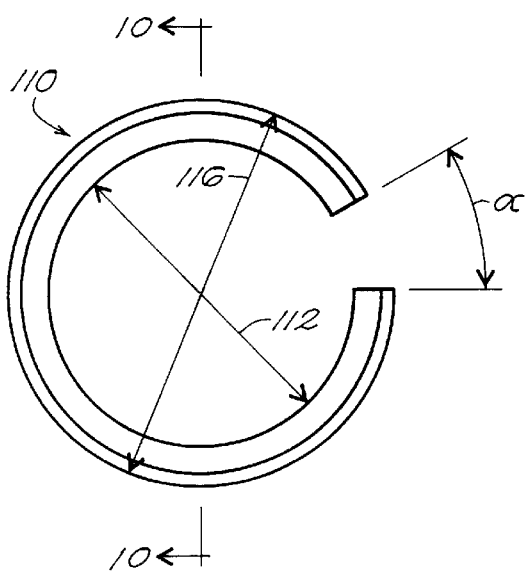
FIG. 9 is a an elevated view of a connecting element of the invention.
Figure 10:
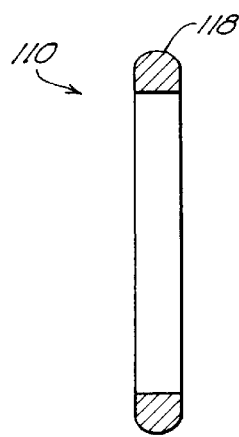
FIG. 10 is a cross-sectional view of the connecting element of FIG. 9 taken along line 10—10.
Figure 11:
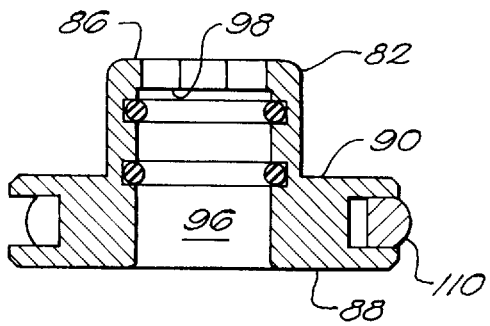
FIG. 11 is a cross-sectional view of a fixed length adaptor of the invention having a −3 mm offset.
Figure 11A:
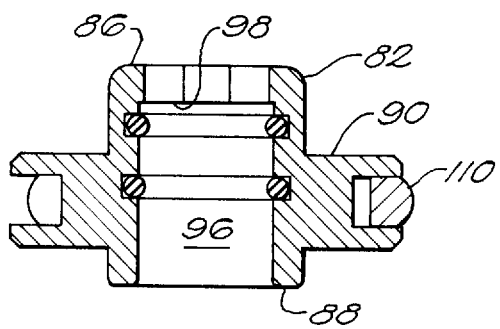
FIG. 11A is a cross-sectional view of a fixed length adaptor of the invention having a 0 mm offset.
Figure 11B:
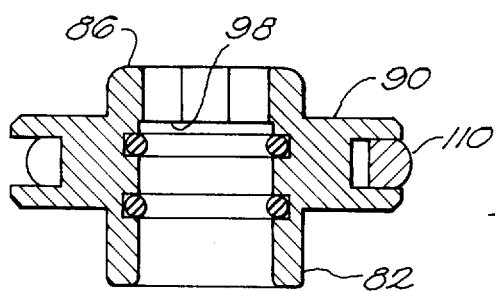
FIG. 11B is a cross-sectional view of a fixed length adaptor of the invention having a +5 mm offset.
Figure 11C:
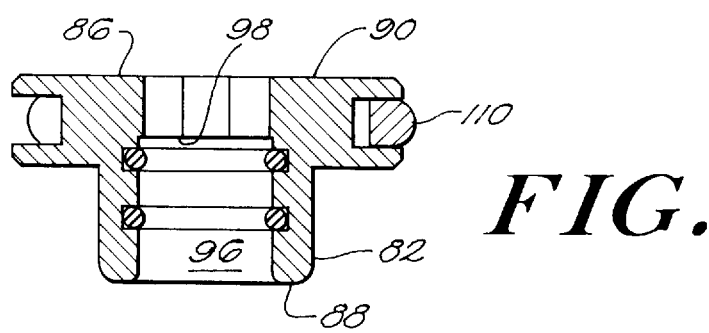
FIG. 11C is a cross-sectional view of a fixed length adaptor of the invention having a +10 mm offset.

In a preferred embodiment, flange portion 90 has a groove 108 about its outer circumference suitable for seating a resilient connecting element 110. The connecting element 110, in an embodiment illustrated in FIGS. 9 and 10, is an arc member having an inner diameter 112 that exceeds the diameter $D_1$ the groove 108 so that, when the connecting element 110 is in an a first, unflexed position, a clearance 114 (shown in FIG. 8) exists between the groove 108 and the connecting element 110. The nominal (unflexed) outer diameter 116 of the connecting element 110 also exceeds the outer diameter $D_2$ of the flange portion 90, preferably by about 0.05 to 0.11 inch.

The connecting element 110 is made from a flexible material so that the arc may be compressed from a first, unflexed position to a second, compressed position wherein the connecting element 110 maintains a second outer diameter that is less than its nominal outer diameter 116 in response to a compressive force such as when the adaptor 80 is pressed into the shell trial 60. The exemplary connecting element 110 may be formed as a complete ring, but a portion corresponding to an angle α is preferably removed from the connecting element 110. The removed portion α may generally be an arc of between about 10° to 60°, and preferably is an arc of about 30°.

One of ordinary skill in the art will readily appreciate that the connecting element 110 may be made from a variety of resilient materials that possess shape memory. Such materials include polymeric materials as well as metallic materials. Exemplary materials include acetal copolymer, polyethylene, polypropylene, polyphenyl sulfone and nylon.

When the adaptor 80 is inserted into the shell 60, contact forces from the inner cavity 65 of the shell trial 60 compress the resilient connecting element 110 from its first, nominal outer diameter 116 to its second, compressed outer diameter and the adaptor 80 slides into the shell trial 60. When the flange portion 90 meets the annular shelf 72 within the shell trial opening 64, the connecting element 100 correspondingly becomes aligned with the annular groove 70 and the resilient connecting element 110 expands to mate with the groove 70 and thereby secures the adaptor 80 to the shell trial 60. The connecting element 110 preferably has a rounded outer edge 118 configured to correspond to the shape of the annular groove 70 to facilitate mating therewith.

The fixed length trial adaptor 80 may be removed from a shell trial by inserting an appropriate tool through the apical hole 67 in the shell trial as described with respect to the adjustable length adaptor 10. The adaptor 80 may further be provided with an oblong opening 120 on its superior end 86. A tool (not shown) having a cylindrical insertion member and a cross member proximate to its insertion end may be inserted through the oblong opening 120 from the inferior side with the cross-member aligned with the oblong hole 120. The tool may then be rotated 90° so that the cross member is no longer aligned with the oblong hole 120. The adaptor 80 can then be separated from the shell 60 by pulling on the tool with sufficient force to compress the resilient connecting element 110 and remove the adaptor 80.

Trials of various neck trunnions may be simulated using fixed length trial adaptors having different effective lengths. The effective length of the trial adaptor 80 may be varied, for example, by locating the circumferential flange portion 90 at different positions along the barrel member 82. The location of the end region 98 of the barrel's internal cavity 96 may also be varied to this effect. Fixed length trial adaptors 80 having relative effective lengths of −3 mm, 0 mm, +5 mm and +10 mm are illustrated in FIGS. 11, 11A, 11B and 11C, respectively.

A physician may elect during surgery to convert the bipolar shell trial into a unipolar head by inserting the adjustable length unipolar trial adaptor 10 or the fixed length unipolar trial adaptor 80 into shell 60. Use of either adaptor allows a physician to adjust the fit of the head or the bipolar shell and reduce the femur while electing the appropriate neck length without the usual cumbersome bipolar trial system.

The trial system preferably includes various bipolar shell sizes and various femoral stem sizes to allow the surgeon to select the appropriate size while performing a trial reduction. Where fixed length adaptors 80 are used, the trial system preferably includes a plurality of adaptors 80 representing different relative neck lengths.

Although the present invention is described with respect to particular embodiments and features and uses, numerous variations or equivalents are possible without taking away from the spirit or scope of the claimed invention. All references cited herein are expressly incorporated by reference in their entirety.

What is claimed is:

1. A fixed length femoral head trial adapter for converting a shell trial to a head trial, comprising:

a generally cylindrical barrel member having an outer surface with superior and inferior ends, an inner surface defining a cavity for receiving a neck trunnion of a femoral stem trial and a circumferential flange disposed on the outer surface and having an outer diameter sized to fit the shell trial; and a resilient connecting element disposed on the circumferential flange, the connecting element having a nominal first diameter compressible to a second, smaller diameter in response to a force and returnable to the nominal first diameter in the absence of the force for securing the trial adaptor to a shell trial.

2. The adaptor of claim 1, further comprising a circumferential groove formed in the flange.

3. The adaptor of claim 2, wherein the connecting element is made from an acetal copolymer.

4. The adaptor of claim 2, wherein the connecting element is disposed within the circumferential groove on the flange.

5. The adaptor of claim 4, wherein the nominal first diameter of the connecting element is greater than the outer diameter of the flange.

6. The adaptor of claim 5, wherein the connecting element is shaped to mate with a corresponding annular groove within the shell trial.

7. The adaptor of claim 1, wherein the connecting element is an arc member.

8. The adaptor of claim 7, wherein the arc defines an angle of less than 360°.

9. The adaptor of claim 1, wherein the flange is located at a predetermined position along the outer surface of the barrel member between the superior and inferior ends so as to simulate a neck trial of a given length.

10. A femoral head trial adapter system for converting a shell trial to a head trial comprising:

at least one generally cylindrical barrel member having an outer surface with superior and inferior ends, an inner surface defining a cavity for receiving a neck trunnion of a femoral stem trial and a circumferential flange portion disposed on the outer surface of the barrel member, the flange portion having an outer diameter and a circumferential groove; and a resilient connecting element for securing the trial adaptor to a shell trial, the connecting element disposed within the circumferential groove of the flange portion and having a nominal first diameter that is compressible to a second, smaller diameter in response to a force and returnable to the nominal first diameter in the absence of the force, the nominal first diameter being greater than the outer diameter of the flange portion.

11. The system of claim 10, wherein the connecting element is compressible within the groove of the flange portion.

12. The system of claim 10, wherein the connecting element is shaped to mate with a corresponding groove within the shell trial.

13. The system of claim 12, wherein the connecting element defines an arc of less than 360°.

14. The system of claim 13, wherein the connecting element defines an arc of between about 300° to 350°.

15. The system of claim 10, wherein the flange portion is disposed at a predetermined location on the outer surface of the barrel member between the superior and inferior ends thereof.

16. The system of claim 15, wherein the system comprises a plurality of barrel members having flange portions disposed at different predetermined locations on the outer surface of the barrel members.

17. A femoral trial system comprising:

a femoral stem trial including a neck portion;

a shell trial having a bone contacting outer surface and a non-bone contacting inner surface defining a cavity; and a fixed length adaptor removably attachable to the neck portion and to the inner surface of the shell trial for converting a shell trial to a head trial, the fixed length adaptor including:

a generally cylindrical barrel member having an outer surface with superior and inferior ends, an inner surface defining a cavity for receiving the neck portion and a circumferential flange disposed on the outer surface of the barrel member, the circumferential flange having an outer diameter and having a groove formed therein; and a resilient connecting element for securing the trial adaptor to the shell trial, the resilient connecting element being disposed on the circumferential flange and having a nominal first diameter compressible to a second, smaller diameter in response to a force and returnable to the first diameter in the absence of the force.

18. The trial system of claim 17, further comprising an annular groove formed within the cavity of the shell trial.

19. The trial system of claim 18, wherein the connecting element comprises an arc member.

20. The trial system of claim 19, wherein the arc member is less than 360°.

21. The trial system of claim 20, wherein the arc member is disposed within the groove of the circumferential flange.

22. The trial system of claim 20, wherein the nominal first diameter of the connecting element is greater than the outer diameter of the circumferential flange.

23. The trial system of claim 20, wherein the connecting element is compressible within the groove of the circumferential flange.

24. The trial system of claim 20, wherein the connecting element is shaped to mate with the annular groove within the cavity of the shell trial.

25. The trial system of claim 20, wherein the flange is located at a predetermined position along the outer surface of the barrel member, between the superior and inferior ends thereof, to simulate a neck trial of a given length.

* * * * *